(12) United States Patent
Weiss

(10) Patent No.: US 9,980,675 B2
(45) Date of Patent: May 29, 2018

(54) SYSTEM AND METHOD FOR BIOLOGICAL APPLICATIONS USING PRE-DETERMINED SIZED NANOPARTICLES

(71) Applicant: ARkival Technology Corp., Nashua, NH (US)

(72) Inventor: Ronald D. Weiss, Nashua, NH (US)

(73) Assignee: Arkival Technology Corp., Nashua, NH (US)

( * ) Notice: Subject to any disclaimer, the term of this patent is extended or adjusted under 35 U.S.C. 154(b) by 27 days.

(21) Appl. No.: 15/342,262

(22) Filed: Nov. 3, 2016

(65) Prior Publication Data

US 2017/0071535 A1    Mar. 16, 2017

Related U.S. Application Data

(62) Division of application No. 14/832,319, filed on Aug. 21, 2015, now Pat. No. 9,510,767.

(51) Int. Cl.
*A61B 5/055*    (2006.01)
*A61B 5/00*    (2006.01)
(Continued)

(52) U.S. Cl.
CPC .......... *A61B 5/4839* (2013.01); *A61B 5/0035* (2013.01); *A61B 5/055* (2013.01);
(Continued)

(58) Field of Classification Search
CPC .......... A61B 2562/0285; A61B 5/0035; A61B 5/0515; A61B 5/055; A61B 5/4839;
(Continued)

(56) References Cited

U.S. PATENT DOCUMENTS

| 8,486,720 B2 | 7/2013 | Banerjee et al. |
| 8,700,124 B2 | 4/2014 | Weiss et al. |

(Continued)

OTHER PUBLICATIONS

R.E. Rosensweig, et al. "Study of Ferromagnetic Liquid", Mar. 1967, Office of Advanced Research and Technology, National Aeronautics and Space Administration, Contractor Report #91684, 241 pages, see pp. 76-89 and 90-115.

(Continued)

*Primary Examiner* — Mark Remaly
(74) *Attorney, Agent, or Firm* — Preti Flaherty Beliveau & Pachios LLP

(57) ABSTRACT

The invention features an apparatus for producing a fluid stream having plurality of nanoparticles in the fluid stream. The apparatus includes a source configured to provide a fluid stream having a first randomly sized distribution of a plurality of nanoparticles; a flow control zone configured to receive the fluid stream from the source and to control the fluid stream to produce a controlled fluid stream having a selected flow rate; a separation zone configured to receive and to separate the selectively controlled fluid stream into at least one separated fluid stream having a non-randomly sized distribution of nanoparticles; and a collection zone capable of receiving the separated fluid stream according to at least one non-random sized distribution of nanoparticles to produce at least one collected stream. The apparatus is configured for a continuous flow of the fluid stream. A size of a nanoparticle can be related to an intrinsic core diameter, a hydrodynamic diameter, and a combination of intrinsic core diameter and hydrodynamic diameter measurements. The nanoparticles can include non-magnetic nanoparticles, partially magnetic nanoparticles, magnetic nanoparticles, superparamagnetic nanoparticles, and a combination of at least two different nanoparticle types. The invention also features methods for producing said fluid streams. The (Continued)

invention further features apparatus and methods for cancer confirmation and targeted therapeutic drug development.

16 Claims, 10 Drawing Sheets

(51) Int. Cl.
    *A61B 5/05*     (2006.01)
    *A61K 49/00*     (2006.01)
    *A61K 49/18*     (2006.01)
    *B03C 1/30*     (2006.01)
    *B03C 1/025*     (2006.01)

(52) U.S. Cl.
    CPC .......... *A61B 5/0515* (2013.01); *A61B 5/7246* (2013.01); *A61K 49/0002* (2013.01); *A61K 49/1818* (2013.01); *B03C 1/025* (2013.01); *B03C 1/30* (2013.01); *A61B 2562/0285* (2013.01); *B03C 2201/18* (2013.01); *B03C 2201/26* (2013.01)

(58) Field of Classification Search
    CPC .............. A61B 5/7246; A61K 49/0002; A61K 49/1818; B03C 1/30
    See application file for complete search history.

(56) References Cited

U.S. PATENT DOCUMENTS 8,855,740 B1     10/2014     Weiss et al.
2011/0059550 A1     3/2011     Haik

OTHER PUBLICATIONS

Ronald D. Weiss, et al. "Development of MRI-based Diagnostics to Assess the Enhanced Permeability and Retention Effect in Solid Tumors to Guide Optimal Use of Nanoscale Therapeutics" NanoSciTech Open Library, vol. 1, Issue 1, 2015, pp. 12-21.

SYSTEM AND METHOD FOR BIOLOGICAL APPLICATIONS USING PRE-DETERMINED SIZED NANOPARTICLES

STATEMENT REGARDING FEDERALLY SPONSORED RESEARCH OR DEVELOPMENT

Not applicable.

BACKGROUND OF THE INVENTION

Nanoparticle ("NP") applications in medical diagnostics and other investigative and therapeutic technologies represent novel and improved modes of in-situ, internal, cell and tissue diagnostics and targeted drug delivery. Nanoparticles can be administered systemically to a subject, such as a human body. The small nanometer size of nanoparticles allows nanoparticle entry into internal subsurface regions and functional areas that cannot be achieved and observed by conventional means.

Magnetic nanoparticles ("MNPs") can be directed to a particular target in a subject through the use of an external magnetic field and/or via the target's systemic system. Accordingly, magnetic nanoparticles have been used in non-invasive, in situ diagnostics, such as, for a non-limiting example, magnetic resonance imaging ("MRI"). In addition, magnetic nanoparticles have been used in targeted drug delivery applications. For example, a therapeutic agent can be attached to a surface of a targeted nanoparticle. Alternatively, a therapeutic agent can be contained within a polymer coating encapsulating an intrinsic core of the targeted nanoparticle. Ultimately, the magnetic nanoparticles can be localized in the systemic system through the application of the magnetic field and/or ultrasound and/or the natural systemic flow within the system.

The enhanced permeability and retention ("EPR") effect, where molecules of certain sizes tend to accumulate notably more in tumor tissues than in normal tissues, can be related to nanoparticle applications. Only molecules and accordingly, nanoparticles, of certain sizes can enter or permeate or be retained by cancerous cells and tissue. The EPR effect is one of the most exploitable known dynamics in the delivery of systemically administered drugs to cancerous tissues, because the dynamic relates to the anatomical and pathophysiological features of tumor blood vessels. Macromolecular cancer drug developers identify the EPR effect as the predominant mechanism for targeting drugs to solid tumors. Personalized medicine approaches can extend to noninvasive methods for predicting and measuring therapeutic responses based on the exploitability of the EPR effect.

To date, the EPR effect has not been sufficiently exploited in nanoparticle medical applications because typically the applications employ randomly sized distributions of nanoparticles and fail to correlate nanoparticle size to EPR effect for maximum entry and retention of nanoparticles by cancerous cells and tissue. In addition, typical nanoparticle medical applications fail to consider that the EPR effect is not homogeneous and can vary from patient to patient, tumor to tumor, and even within a single tumor.

Thus, there is a need to develop systems and methods for using predetermined, closely sized and/or non-randomly sized distributions of nanoparticles to provide greater insight into cell and tissue functioning, to improve the efficiency and efficacy of EPR related diagnostics and therapies, and to reduce side effects compared to conventional treatments.

BRIEF SUMMARY OF THE INVENTION

The present invention involves systems and methods to produce pre-determined, closely sized, segregated, non-randomly sized distributions of nanoparticles for novel and improved nanoparticle medical applications including, but not limited to, medical diagnostics and targeted drug delivery, and the understanding of cell functionality particularly related to the EPR effect. For purposes of this application, a "non-randomly sized distribution" is defined as a subset of a randomly sized distribution of nanoparticles where the statistical range of nanoparticle sizes and/or the nanoparticle size distribution is narrower as compared to the larger randomly sized distribution of nanoparticles. The invention exploits the EPR effect where cancerous cells have different permeability and retention rates depending upon the size of molecules, and accordingly, nanoparticles. The invention correlates predetermined, narrowly sized distributions of nanoparticles to EPR effects to confirm or deny the presence of cancer, thereby eliminating false cancer positives and negatives in medical diagnostics. The invention further features therapeutic drug development based on the correlation of size to EPR effect to maximize the delivery of the therapeutic drug to its target. The nanoparticles can include non-magnetic, partially magnetic, fully magnetic and superparamagnetic nanoparticles, and combinations thereof, depending upon the application.

In one aspect, the invention features an apparatus for producing a fluid stream having plurality of nanoparticles in the fluid stream. The apparatus includes a source configured to provide a fluid stream having a first randomly sized distribution of a plurality of nanoparticles; a flow control zone configured to receive the fluid stream from the source and to control the fluid stream to produce a controlled fluid stream having a selected flow rate; a separation zone configured to receive and to separate the selectively controlled fluid stream into at least one separated fluid stream having a non-randomly sized distribution of nanoparticles; and a collection zone capable of receiving the separated fluid stream according to the at least one non-random sized distribution of nanoparticles to produce at least one collected stream. The apparatus is configured for a continuous flow of the fluid stream. A size of a nanoparticle is related to one of or selected from a group of nanoparticle size measurements including an intrinsic core diameter, a hydrodynamic diameter, and a combination of intrinsic core diameter and hydrodynamic diameter measurements. The nanoparticles are selected from a group of nanoparticle types consisting of non-magnetic nanoparticles, partially magnetic nanoparticles, magnetic nanoparticles, superparamagnetic nanoparticles, and a combination of at least two of the aforementioned different nanoparticle types.

In one embodiment, the apparatus further includes a recycling zone capable of receiving the separated fluid stream prior to the collection zone, and syphoning and recycling at least a first recycling portion of the separated fluid stream back to the fluid stream provided from the source prior to the fluid stream entering the flow control zone.

In another embodiment, the flow control zone further includes an element capable of controlling the fluid stream according to a viscosity of the fluid stream. In still another embodiment, the flow control is adapted for control by a flow control computer.

In one embodiment, the separation zone includes at least one non-magnetic separation system. In other embodiments, the non-magnetic separation system can include one or more mechanical pre-filtering mechanical separation systems, one or more gravitational filtering mechanical separation systems, on or more liquid chromatography separations, and a combination of two or more of the aforementioned non-magnetic separation systems.

In another embodiment, the separation zone includes at least one magnetic separation system. In other embodiments, the magnetic separation system can include one or more static magnetic separation systems configured to produce a uniform magnetic field, one or more pulsating direct current magnetic separation systems configured to produce a pulsed magnetic field and having current flowing in one direction, one or more pulsating alternating current magnetic separation systems configured to produce a pulsed magnetic field having current flowing in alternating directions, one or more variable gradient magnetic separation elements configured to produce at least two magnetic fields having different gradients, and a combination of at least two of the aforementioned magnetic separation systems. In a preferred embodiment, the separation zone includes at least one high gradient magnetic separation system.

In an additional embodiment, the apparatus includes a computer implemented magnetometry system capable detecting, determining and recording at least one first statistical parameter corresponding to a size and size distribution of the nanoparticles in a sample of the fluid stream, wherein the size and size distribution is defined by a computer implemented magnetometry method. The method employs the following steps: performing a magnetic measurement analysis of the sample and generating magnetization data therefrom; determining an asymptotic portion of high field data from the magnetization data for each of four branches (A,B,C,D) as $M_H$ vs. 1/H where $M_H$ is the measured magnetization in a magnetic field of intensity H approaching its saturation value; performing a linear regression analysis of the data in each branch and generating a first correlation curve of the form $M_H=\alpha/H+\beta$; calculating both a number average particle volume, $\tilde{V}_n$, and a saturation magnetization, $M_{sat}$, of the sample, as a function of the first correlation curve; combining low field, linear data of $M_H$ for branches A and C, and branches B and D, and obtaining two plots of $M_H$ vs. H for values of H within a range from −50 Oe to +50 Oe; performing a linear regression analysis of the data in each branch combination and generating a second correlation curve of the form $M_H=\gamma H+\delta$; calculating a volume average particle volume $\tilde{V}_v$ as a function of the saturation magnetization value $M_{sat}$ obtained from the high field measurements, and using the value of the slope γ for the ratio of $M_H/H$; calculating a volume average spherical equivalent magnetic particle diameter $\check{D}_v$ and a number average spherical equivalent magnetic particle diameter $\check{D}_n$ as a function of $\tilde{V}_v$ and $\tilde{V}_n$; and calculating a particle diameter dispersity value, $Đ_d$, of the sample, as a function of the diameter values $\check{D}_v$ and $\check{D}_n$. The nanoparticles can include a plurality of at least partially magnetic nanoparticles. The at least one first statistical parameter can include at least one of a statistical mean size of the nanoparticles, a standard size deviation of the nanoparticles, a statistical size range of the nanoparticles, and the particle diameter dispersity value of the nanoparticles.

In a further embodiment, the apparatus can include a computer controlled monitoring system capable of detecting, determining and recording the at least one first statistical parameter corresponding to the nanoparticles circulating in the fluid stream according to at least one monitoring parameter. The monitoring parameter can include one or more test locations in the apparatus, one or more process times, and a combination of two or more monitoring parameters.

In still a further embodiment, the apparatus can include a comparison system configured for comparing the at least one first statistical parameter with a corresponding at least one second statistical parameter corresponding to a second size and distribution of the nanoparticles circulating in the fluid stream as detected and determined by a non-magnetometry measurement. The comparison system is configured for calibrating the at least one first statistical parameter based on the comparison.

In an additional embodiment, upon introduction into a subject, the collected stream is characterized as having a distinguishable behavior as compared to the fluid stream having the first randomly sized distribution of nanoparticles.

In another aspect, the invention features a diagnostic apparatus. The diagnostic apparatus includes a diagnostic panel including at least two tracer solutions configured for introduction into a subject. Each of the tracer solutions has a non-randomly sized distribution of a plurality of nanoparticles. Each of the non-randomly sized distributions corresponds to at least one first statistical parameter selected from the group consisting of a statistical mean size of the nanoparticles, a standard deviation of the sizes of the nanoparticles, a statistical size range of the nanoparticles, a particle diameter dispersity value of the nanoparticles, and a combination of at least two of the aforementioned first statistical parameters. A size of a nanoparticle can be related to one of a group of nanoparticle size measurements including an intrinsic core diameter, a hydrodynamic diameter, and a combination of an intrinsic core diameter and a hydrodynamic diameter. The nanoparticles are selected from a group of nanoparticle types consisting of non-magnetic nanoparticles, partially magnetic nanoparticles, magnetic nanoparticles, superparamagnetic nanoparticles, and a combination of at least two different nanoparticle types.

In one embodiment, the tracer solutions are organized in the diagnostic panel in a selected order according to at least one first statistical parameter for a sequential introduction into the subject according to the selected order.

In another embodiment, the diagnostic apparatus further comprises a measurement system, wherein the selected order and the sequential introduction of the tracer solutions in the selected order is adapted for a non-invasive detection of at least one in situ measurement in the subject with the measurement system. The in situ measurement is selected from the group of in situ measurements consisting of a size based ingestion rate of the nanoparticles by the subject, a size based mapping of locations of the nanoparticles in the subject, a size based take up rate of the nanoparticles by the subject, a size based flow rate of the nanoparticles through the subject, a retention rate of the nanoparticles by the subject, a progression profile of a size of a physical structure in the subject, a progression profile of a size of a defect in the subject, and a combination of two or more in situ measurements.

In still another embodiment, the diagnostic apparatus includes a cancer confirmation system configured for confirming a presence or an absence of a cancer in the subject based upon a confirmation method. The confirmation method includes the steps of correlating the in situ measurement with a presence of at least one EPR function or an absence of the EPR function in the subject; and confirming a presence or an absence of a cancer in the subject based upon the correlation of the in situ measurement with, respectively, the presence or the absence of the EPR function. The EPR function is selected from a group of functions consisting of an altered vasculature sizing, an altered vasculature opening, an altered vascular pathway, an extravasation of a tissue, an uptake of the nanoparticles, a retention of the nanoparticles, a densification of a tissue, a size based change in a fluid flow rate of the nanoparticles, a non-homogeneous physical change in the subject, and a combination of two or more functions.

In an additional embodiment, the diagnostic apparatus includes a therapeutic drug designing system configured for sizing a therapeutic drug based upon a designing method. The designing method includes the steps of: correlating the in situ measurement with a presence of at least one EPR function in the subject; determining a geometric profile of a target tissue having the EPR function based upon the in situ measurement; and matching a physical dimension of a therapeutic agent molecule with the geometric profile of the target tissue having the EPR function to optimize delivery of the molecule to the target tissue. The EPR function is selected from a group of functions consisting of an altered vasculature sizing, an altered vasculature opening, an altered vascular pathway, an extravasation of a tissue, an uptake of the nanoparticles, a retention of the nanoparticles, and a densification of a tissue, a size based change in a fluid flow rate of the nanoparticles, a non-homogeneous physical change in the subject, and a combination of two or more of the aforementioned functions.

In another aspect, the invention features a method for producing a fluid stream having a plurality of nanoparticles in the fluid stream. The method includes providing a source of the fluid stream, wherein the fluid stream includes a first randomly sized distribution of the nanoparticles; receiving the fluid stream from the source in a flow control zone, and controlling the fluid stream to produce a controlled fluid stream having a selected flow rate; receiving in a separation zone and separating the controlled fluid stream into at least one separated fluid stream having a non-randomly sized distribution of nanoparticles; and receiving in a collection zone the separated fluid stream according to the at least one non-randomly sized distribution of nanoparticles to produce at least one collected stream. The fluid stream flows continuously. A size of a nanoparticle is related to at least one of a group of nanoparticle size measurements including an intrinsic core diameter, a hydrodynamic diameter, and a combination of intrinsic core and hydrodynamic diameters. The nanoparticles are selected from a group of nanoparticle types consisting of non-magnetic nanoparticles, partially magnetic nanoparticles, magnetic nanoparticles, superparamagnetic nanoparticles, and a combination of at least two different nanoparticle types.

In one embodiment, the method further includes receiving the separated fluid stream in a recycling zone disposed prior to the collection zone; and syphoning at least a first recycling portion of the separated fluid stream and recycling the first recycling portion back to the fluid stream entering the flow control zone.

In another embodiment, the flow control zone featured in the method of the invention includes an element capable of controlling the fluid stream according to a viscosity of the fluid stream. In still another embodiment, the flow control zone is adapted for control by a flow control computer.

In a further embodiment, the separation zone featured in the method of the invention includes at least one non-magnetic separation system. The non-magnetic separation system can include one or more mechanical pre-filtering mechanical separation systems, one or more gravitational filtering mechanical separation systems, one or more liquid chromatography separation systems, and combinations of two or more non-magnetic separation systems.

In another embodiment, separation zone featured in the method of the invention includes at least one magnetic separation system. The magnetic separation system can include one or more static magnetic separation systems configured to produce a uniform magnetic field, one or more pulsating direct current magnetic separation systems configured to produce a pulsed magnetic field and having current flowing in one direction, one or more pulsating alternating current magnetic separation systems configured to produce a pulsed magnetic field having current flowing in alternating directions, one or more variable gradient magnetic separation systems configured to produce magnetic fields having at least two different gradients, and combinations of at least two magnetic separation systems. In a preferred embodiment, the magnetic separation system featured in the method of the invention includes a high gradient magnetic separation system.

In another embodiment, the method of the invention further includes detecting, recording and communicating at least one first statistical parameter corresponding to a first size and size distribution of the nanoparticles as defined by a computer implemented magnetometry method. The computer implemented magnetometry method includes performing a magnetic measurement analysis of the sample and generating magnetization data therefrom; determining an asymptotic portion of high field data from the magnetization data for each of four branches (A,B,C,D) as $M_H$ vs. $1/H$ where $M_H$ is the measured magnetization in a magnetic field of intensity H approaching its saturation value; performing a linear regression analysis of the data in each branch and generating a first correlation curve of the form $M_H = \alpha/H + \beta$; calculating both a number average particle volume, $\tilde{V}_n$, and a saturation magnetization, $M_{sat}$, of the sample, as a function of the first correlation curve; combining low field, linear data of $M_H$ for branches A and C, and branches B and D, and obtaining two plots of $M_H$ vs. H for values of H within a range from −50 Oe to +50 Oe; performing a linear regression analysis of the data in each branch combination and generating a second correlation curve of the form $M_H = \gamma H + \delta$; calculating a volume average particle volume $\hat{V}_v$ as a function of the saturation magnetization value $M_{sat}$ obtained from the high field measurements, and using the value of the slope γ for the ratio of $M_H/H$; calculating a volume average spherical equivalent magnetic particle diameter $\check{D}_v$ and a number average spherical equivalent magnetic particle diameter $\check{D}_n$ as a function of $\hat{V}_v$ and $\hat{V}_n$; and calculating a particle diameter dispersity value, $Đ_{d_c}$ of the sample, as a function of the diameter values $\check{D}_v$ and $\check{D}_n$. The nanoparticles include a plurality of at least partially magnetic nanoparticles. The at least one first statistical parameter includes at least one of a statistical mean size of the nanoparticles, a standard deviation of the sizes of the nanoparticles, a statistical size range of the nanoparticles, and the particle diameter dispersity value of the nanoparticles.

In a further embodiment, the method includes detecting, recording and communicating with a computer controlled monitoring system the at least one first statistical parameter corresponding to the nanoparticles circulating in the fluid stream according to at least one monitoring parameter. The monitoring parameter can include one or more test locations in the apparatus, one or more process times, and a combination of two or more of the aforementioned monitoring parameters.

In still a further embodiment, the method includes comparing the at least one first statistical parameter with a corresponding at least one second statistical parameter corresponding to a second size and distribution of the nanoparticles circulating in the fluid stream as detected and determined by a non-magnetometry measurement; and calibrating the at least one first statistical parameter based upon the comparison.

In another embodiment, the method includes upon introduction into a subject, the collected stream behaving in a distinguishable manner from the fluid stream having a first randomly sized distribution of nanoparticles.

In an additional aspect, the invention features a method for conducting an in situ measurement in a subject. The method includes providing at least two tracer solutions in a diagnostic panel. Each of the tracer solutions has a non-randomly sized distribution of a plurality of nanoparticles. Each of the non-randomly sized distributions corresponds to at least one first statistical parameter. The at least one first statistical parameter can include a statistical mean size of the nanoparticles, a standard size deviation of the nanoparticles, a statistical size range of the nanoparticles, a particle diameter dispersity value of the nanoparticles, and a combination of at least two of the aforementioned statistical parameters. A size of a nanoparticle is related to one of or selected from a group of nanoparticle size measurements including an intrinsic core diameter, a hydrodynamic diameter, and a combination of an intrinsic core diameter and a hydrodynamic diameter. The nanoparticles can consist of non-magnetic nanoparticles, partially magnetic nanoparticles, magnetic nanoparticles, superparamagnetic nanoparticles, and a combination of at least two different of the aforementioned nanoparticle types. The method of this aspect of the invention further includes introducing sequentially into the subject the tracer solutions in the diagnostic panel according to a selected order based upon the at least one first statistical parameter; and conducting a non-invasive detection of each of the tracer solutions in the subject to determine at least one in situ measurement in the subject. The in situ measurement can include a size based ingestion rate of the nanoparticles by the subject, a size based mapping of locations of the nanoparticles in the subject, a size based take up rate of the nanoparticles by the subject, a size based flow rate of the nanoparticles through the subject, a retention rate of the nanoparticles by the subject, a progression profile of a size of a physical structure in the subject, a progression profile of a size of a defect in the subject, and a combination of two or more of the aforementioned in situ measurements.

In one embodiment, the method further includes correlating the in situ measurement with a presence of at least one EPR function or an absence of the EPR function in the subject; and confirming a presence or an absence of a cancer in the subject based upon the correlation of the in situ measurement with respectively the presence or the absence of the EPR function. The EPR function can include an altered vasculature sizing, an altered vasculature opening, an altered vascular pathway, an extravasation of a tissue, an uptake of the nanoparticles, a retention of the nanoparticles, and a densification of a tissue, a size based change in a fluid flow rate of the nanoparticles, a non-homogeneous physical change in the subject, and a combination of two or more functions.

In still another embodiment, the method can include correlating the in situ measurement with a presence of at least one EPR function in the subject; determining a geometry or a profile of a target tissue having the EPR function based upon the in situ measurement; and matching a physical dimension of a therapeutic agent molecule with the geometric profile of the target tissue having the EPR function to optimize delivery of the molecule to the target tissue; wherein the EPR function can include an altered vasculature sizing, an altered vasculature opening, an altered vascular pathway, an extravasation of a tissue, an uptake of the nanoparticles, a retention of the nanoparticles, and a densification of a tissue, a size based change in a fluid flow rate of the nanoparticles, a non-homogeneous physical change in the subject, and a combination of two or more of the afore-mentioned functions.

BRIEF DESCRIPTION OF THE SEVERAL VIEWS OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION OF THE INVENTION

The entire contents of U.S. Pat. Nos. 8,700,124 and 8,855,740 are incorporated by reference herein for all purposes.

Prior to discussion of the various embodiments of the present invention, a preview discussion of nanoparticle technology is provided. Nanoparticles are available in either liquid or powder forms, and can include non-magnetic, partially magnetic, magnetic and superparamagnetic nanoparticles. A powder including a concentration of nanoparticles can be dispersed or suspended in a liquid solution or other carrier, as needed for an intended application. Nanoparticles can be extracted from the liquid solution or other carrier by the non-limiting methods of evaporation, thermal drying, freeze-drying, fine particle filtration, and other methods known to those of ordinary skill in the art.

Figure 1:
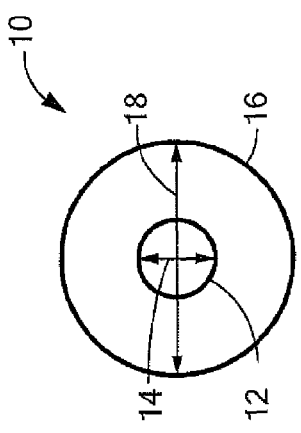
FIG. 1 is a schematic diagram of a nanoparticle.

Typically, a liquid solution or other carrier of dispersed or suspended nanoparticles includes a non-uniform or randomly sized distribution of particles. The particle sizes depend upon the preparation method and the particles' particular chemical formulation. FIG. 1 shows a schematic of a nanoparticle 10. Each nanoparticle 10 has an intrinsic core 12, which is typically spherical, and a defined intrinsic core diameter 14. Each particle 10 also can have a surface coating 16, which surrounds or contains the intrinsic core 12, and has a defined hydrodynamic diameter 18. The hydrodynamic diameter 18 of a particle is considered a measurement of its physical size.

Typically, the sizes of the intrinsic core diameters of nanoparticles can be examined and measured by different types of X-ray diffraction and electron microscopy, such as for non-limiting examples, dynamic light scattering microscopy ("DLS"), transmission electron microscopy ("TEM"), and scanning electron microscopy ("SEM"). The intrinsic core diameter sizes of nanoparticles having a magnetic quality can be additionally examined and measured by magnetometry, as discussed in U.S. Pat. Nos. 8,700,124 and 8,855,740. The sizes of nanoparticles are important in detection methods, such as, for a non-limiting example, magnetic resonance imaging (MRI), and in targeted drug delivery.

The hydrodynamic diameter sizes of nanoparticles are typically examined and measured by laser interferometry. Notably, the hydrodynamic diameter sizes or physical sizes of the nanoparticles are particularly important for the mobility of the nanoparticles and their ability to access particular cells and tissues, which in turn affects nanoparticle behavior and performance.

A measurement of the sizes including the range and distribution of sizes of the intrinsic core diameters and hydrodynamic diameters of nanoparticles can be particularly useful in biological applications including diagnostic, therapeutic, and pharmaceutical applications. Nanotechnology diagnostics and therapeutics including targeted therapeutic delivery are related to the physiochemical attributes of nanoparticles which affect their abilities for attachment, duration, and release, and the effects which result therefrom. A comprehensive understanding of size and size effects of the nanoparticles is fundamental to exploiting the physiochemical attributes of nanoparticles.

The IUPAC Recommendation of 2011 provides a measurement for the size variability of intrinsic core diameters and hydrodynamic diameters in nanoparticles by defining a particle diameter dispersity calculated as the ratio of the volume average particle volume to the number average particle volume.

Statistical parameter data including, for non-limiting examples, a statistical mean size of the nanoparticles, a standard size deviation of the nanoparticles, a statistical size range of the nanoparticles, and/or a particle diameter dispersity value can help to define functionality and potential applications for nanoparticle containing substances. The magnetometry method described in U.S. Pat. No. 8,700,124, can provide a measurement of a size and size distribution of nanoparticles before and after the introduction of the nanoparticles into a subject or other application. The size and size distribution of the nanoparticles including related statistical parameter data can be employed to determine information about internal or intrinsic cells and tissue, including the in situ functionality of organs, tumors, and vascular structure, in accordance with this invention. The magnetometry method of U.S. Pat. No. 8,700,124 describes use of a vibrating sample magnetometer ("VSM") configured for obtaining the necessary magnetization data. It should be noted that other comparable magnetic measurement systems capable of performing similar magnetic measurements and functions can be used, as would be understood by one of ordinary skill in the art, and any reference to a VSM is not intended to be limiting.

In the present invention, the range of sizes, size distribution, and concentration of magnetic nanoparticles in biological matrices can be used to characterize and supplement MRI images of organs, tumors and/or vasculature, and changes thereof. A series or panel of sized nanoparticle tracer solutions including nanoparticles of different but tightly controlled sizes and/or non-randomly sized distributions can be introduced into a subject or other application in sequence with accompanying temporal-based, MRI sequence captures. Such information can be used to match the physical dimensions of a therapeutic agent molecule(s) and/or nanoparticles to the geometry and/or profile of, for a non-limiting example, a tumor vasculature. Further, a non-invasive diagnostic procedure, such as MRI, in conjunction with the introduction of a closely sized and/or non-randomly sized distribution of nanoparticles can serve as an adjunct or replacement for biopsies, such as for a non-limiting example, tumor biopsies, and/or provide detailed information for personalized target specific therapeutic drug delivery.

The present invention also provides a noninvasive technique for an assessment of the EPR effect. This assessment can be integrated with the use of MRI in the workup and staging of cancer patients in a clinic. Magnetic nanoparticle tracers or tracer solutions including closely sized and/or non-randomly sized distributions of nanoparticles that correspond to hydrodynamic dimensions of current nanoscale chemotherapeutics can be prepared to interact in real-time study in tumor models, following systemic administration. A scaled and reproducible process can also be employed to produce statistically distinguishable tracer panels of closely sized and/or non-randomly sized distributions of magnetic nanoparticles suspended or dispersed in liquid or other carrier solutions. Diagnostic guidelines can be established to enhance MRI detection of tumors and provide assistance, direction and technology to developers of targeted therapeutics.

Closely sized and/or non-randomly sized distributions of nanoparticles can also be used in temporal studies and guidelines for tumor uptake, tumor densification profiling ("TDP"), tumor extravasation, and tumor progression profiling based upon delivery of the nanoparticles. Decision criteria based on measurable observations of nano-drug delivery can enhance the tools available for clinicians to determine optimal patient therapies.

Applications of closely sized and/or non-randomly sized distributions of nanoparticles can also be used in applications for identifying true positives and negatives (and conversely minimizing false positives and negatives) in cancer screenings and detection. Using the EPR effect of an exclusive function in cancer only sites, the delivery of the sized magnetic nanoparticles can be used for EPR measurement via MRI, and the measurement and presence of EPR function can indicate false negatives and the potential for growth of further metastases.

Figure 2:
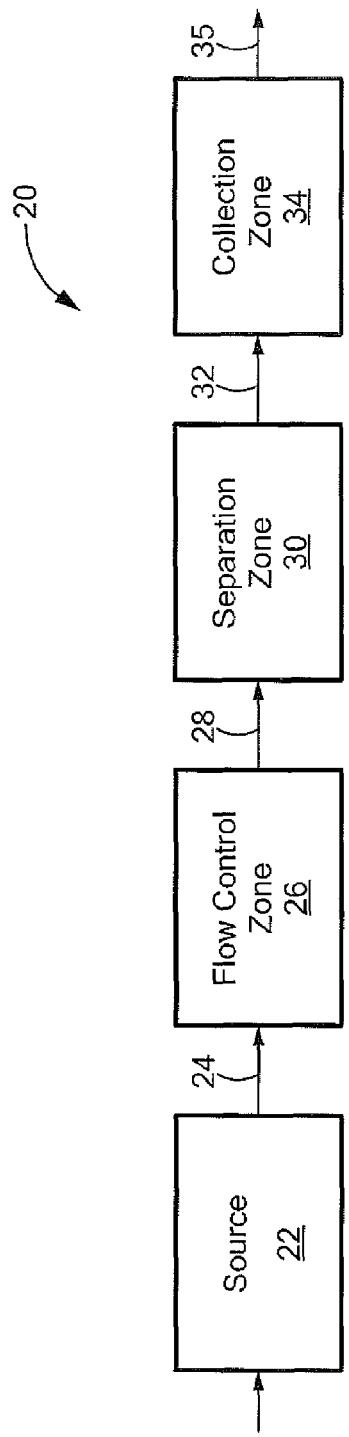
FIG. 2 is a functional block diagram of an embodiment of the present invention.

Referring now to FIG. 2, in one aspect, the present invention provides an apparatus 10 for producing a stream solution of nanoparticles. The apparatus includes a source 22 configured to provide a fluid stream 24 having a first randomly sized distribution of nanoparticles. The fluid stream 24 from the source 22 is directed to a flow control zone 26 configured to receive the fluid stream 24 from the source 22 and to control the fluid stream according to a selected flow rate to produce a selectively controlled fluid stream 28. The controlled fluid stream 28 is then directed to a separation zone 30. The separation zone 30 is configured to receive and to separate or segregate the selectively controlled fluid stream into a separated fluid stream 32 having at least one non-randomly sized distribution of nanoparticles. The separated fluid stream 32 is then fed into a collection zone 34 capable of receiving the separated fluid stream 32 and producing a collected stream 35 segregated according to the at least one, non-randomly sized distribution of nanoparticles.

The apparatus 20 can be configured for a continuous flow of the fluid stream. Thus, the system of the present invention has the capacity to provide sized and/or non-random distributions of nanoparticles on a continuous basis which greatly facilitates the production of the nanoparticles for diagnostic and therapeutic applications. The size of a nanoparticle can refer to nanoparticle size measurements including an intrinsic core diameter, a hydrodynamic diameter, and a combination of intrinsic core diameter and hydrodynamic diameter measurements. The nanoparticles can include non-magnetic, partially magnetic, fully magnetic or superparamagnetic nanoparticles, or combinations thereof, depending upon the application.

The non-randomly sized distribution of nanoparticles can be closely or narrowly sized and have a predetermined nanometer diameter size difference. The nanometer diameter size difference can be calculated on the basis of the intrinsic core diameters or and/or the hydrodynamic diameters. The nanoparticles can be segregated into a range of nanoparticles having a diameter size difference of less than or equal to 20%, and preferably 10%, and more preferably 5% and most preferably 2%.

Figure 3:
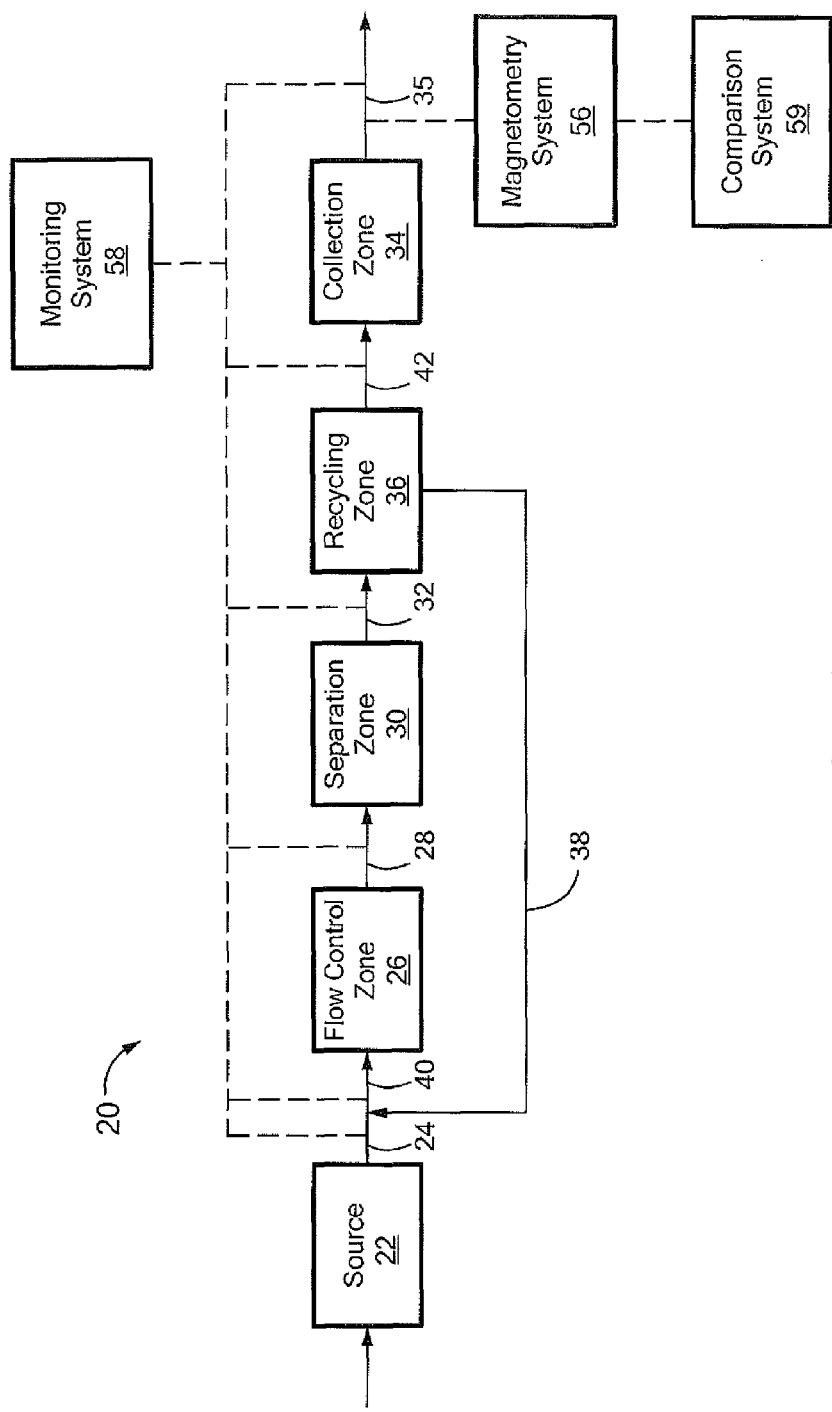
FIG. 3 is a functional block diagram of an embodiment of the present invention.

In one embodiment, the apparatus 10 can include an optional recycling zone 36, as shown in FIG. 3. The recycling zone 36 can receive the separated fluid stream 32 prior to the collection zone 34. The recycling zone 36 can syphon at least a portion 38 of the separated fluid stream and recycle the siphoned portion 38 back to the source fluid stream 24. The combined fluid stream 40 then enters the flow control zone 26. The non-siphoned fluid stream 42 exiting the recycling zone enters the collection zone 34 which produces the collected stream 35 segregated according to the at least one closely sized and/or non-randomly sized distribution of nanoparticles.

Figure 4:
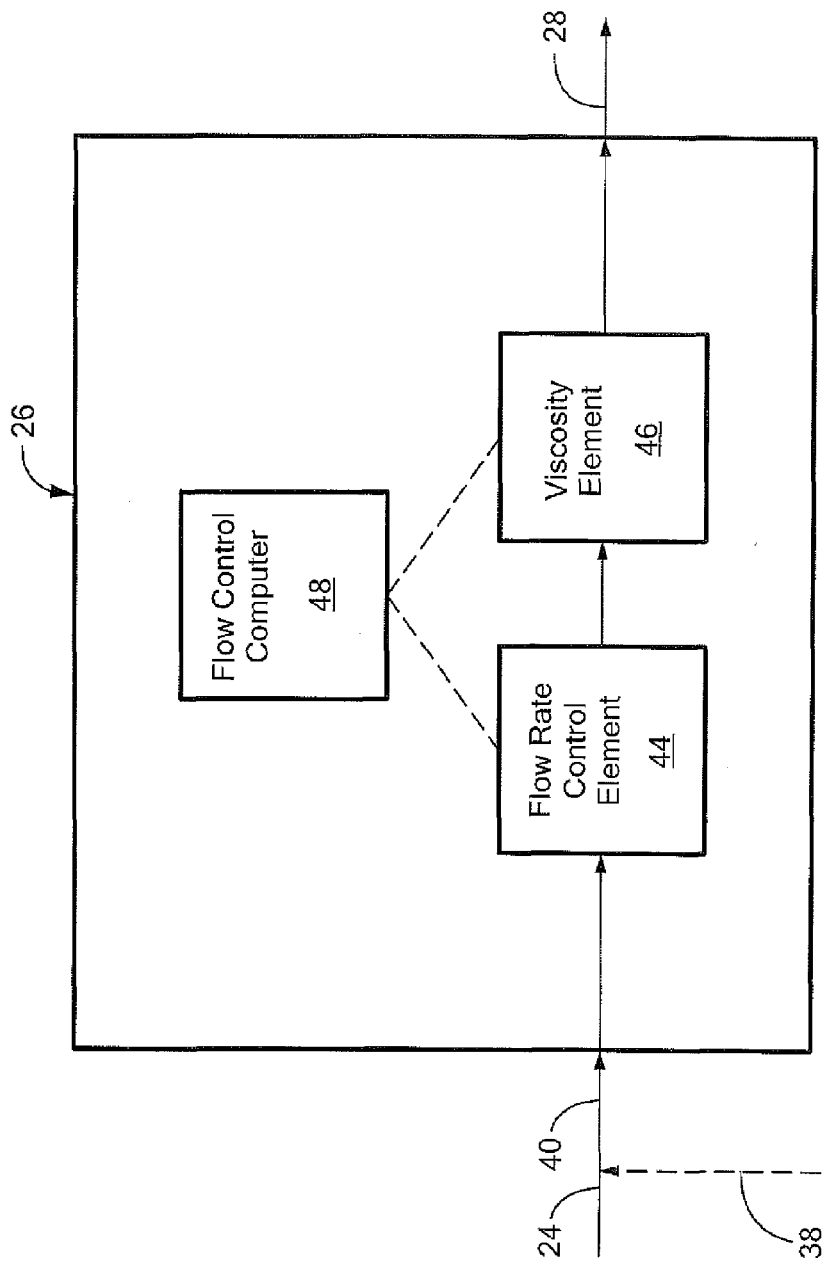
FIG. 4 is a functional block diagram of an embodiment of the present invention.

FIG. 4 shows an exemplary embodiment of the invention wherein the flow control zone 26 includes a flow rate control element 44 capable of controlling a flowrate of the fluid stream, and a viscosity element 46 capable of controlling the fluid stream according to a viscosity of the fluid stream. FIG. 4 also shows the flow control zone 26 is adapted for control by a flow control computer 48 which in turn is configured for communication with the flow rate control element 44 and/or the viscosity element 46.

Figure 5:
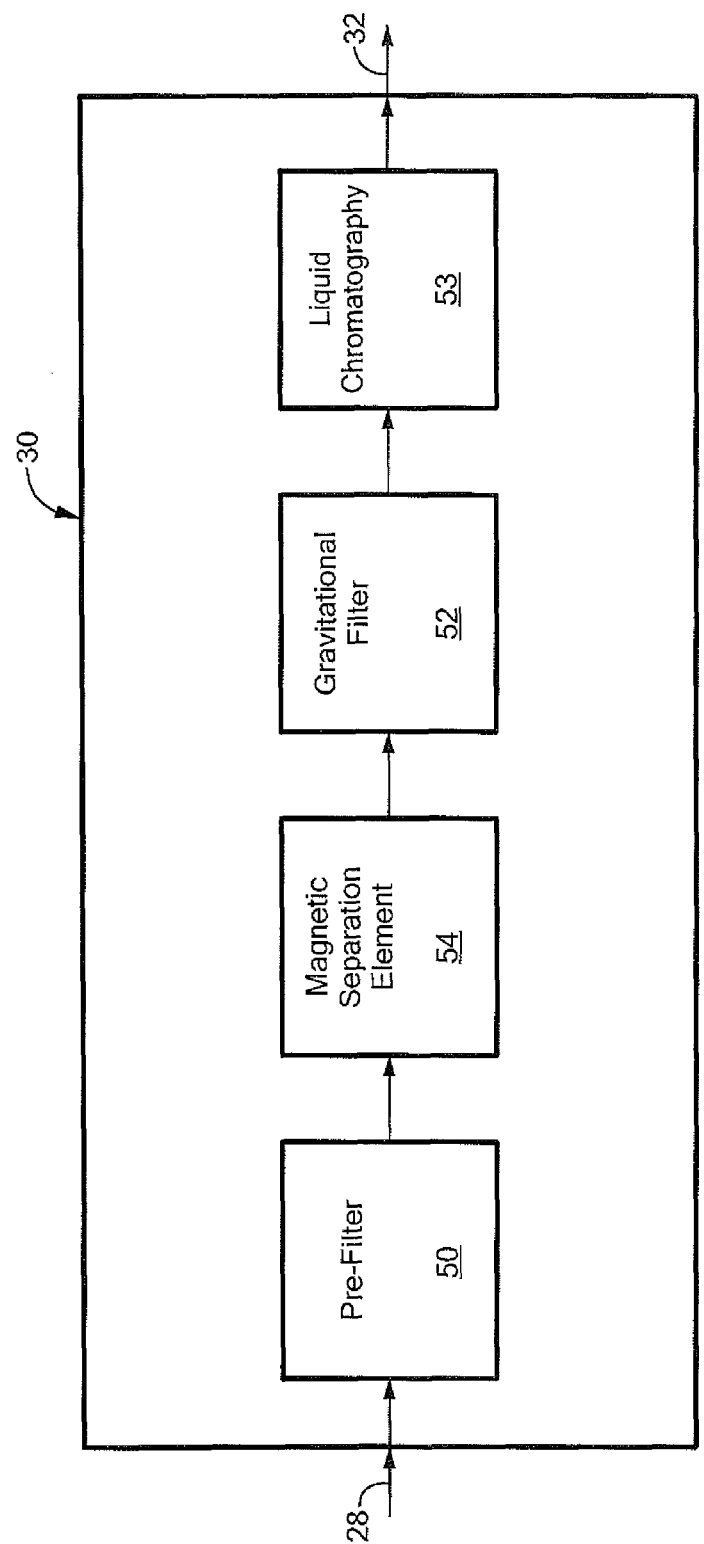
FIG. 5 is a functional block diagram of an embodiment of the present invention.

In different embodiments of the invention, the separation zone 30 can include different types of separation systems, as shown in FIG. 5. For example, the separation zone can include one or more non-magnetic separation systems. The non-magnetic separation systems can also or alternatively include one or more mechanical pre-filters 50 for filtering particulates and/or bacteria from the fluid stream. In other embodiments, the non-magnetic separation systems can include one or more mechanical gravitational filters or stacks of filters 52 and/or include one or more liquid chromatography systems 53 which can produce a separated fluid stream segregated or separated into effluent streams of different sizes or ranges of sizes. The separation zone can also or alternatively include different combinations and orders of at least two similar and/or different non-magnetic separation systems.

In other embodiments, the separation zone 30 can include one or more magnetic separation systems 54. The magnetic separation systems 54 can include one or more static magnetic separation systems wherein each system is configured to produce a constant or uniform magnetic field. The magnetic separation systems 54 can also or alternatively include one or more dynamic or variable magnetic separation systems each configured to produce a dynamic or variable magnetic field. The dynamic or variable magnetic separation systems can include at least one of a pulsating direct current magnetic separation system configured to produce a pulsed magnetic field and having current flowing in one direction (pulsed DC); a pulsating magnetic alternating current separation system configured to produce a pulsed magnetic field and having current flowing in alternating directions (pulsed AC); a magnetic variable gradient separation system configured to produce magnetic fields having different gradients; and a combination of two or more similar or different magnetic separation systems. In a preferred embodiment, the magnetic separation system 54 includes a high gradient magnetic separation ("HGMS") system. For the purposes of this application, a HGMS system is defined as a system capable of adjusting a magnetic field using one or more of the dynamic or variable magnetic separation systems described above. Thus, the separation zone 30 can include different types, numbers, combinations, arrangements, and ordering of separation systems, depending upon the application, as would be understood by one of ordinary skill in the art, and the block diagram shown in FIG. 5 is not intended as limiting.

In one embodiment, FIG. 3 shows that the nanoparticles can include at least partially magnetic nanoparticles and the apparatus 20 can include a computer implemented magnetometry system 56 for determining and recording at least one first statistical parameter corresponding to a first size and size distribution for the nanoparticles in a sample of the fluid stream. The computer implemented magnetometry system 56 can employ a computer implemented magnetometry method for the determination including: performing a magnetic measurement analysis of the sample and generating magnetization data therefrom; determining an asymptotic portion of high field data from the magnetization data for each of four branches (A,B,C,D) as $M_H$ vs. 1/H where $M_H$ is the measured magnetization in a magnetic field of intensity H approaching its saturation value; performing a linear regression analysis of the data in each branch and generating a first correlation curve of the form $M_H = \alpha/H + \beta$; calculating both a number average particle volume, $\tilde{V}_n$, and a saturation magnetization, $M_{sat}$, of the sample, as a function of the first correlation curve; combining low field, linear data of $M_H$ for branches A and C, and branches B and D, and obtaining two plots of $M_H$ vs. H for values of H within a range from −50 Oe to +50 Oe; performing a linear regression analysis of the data in each branch combination and generating a second correlation curve of the form $M_H = \gamma H + \delta$; calculating a volume average particle volume $\tilde{V}_v$ as a function of the saturation magnetization value $M_{sat}$ obtained from the high field measurements, and using the value of the slope γ for the ratio of $M_H/H$; calculating a volume average spherical equivalent magnetic particle diameter $\check{D}_v$ and a number average spherical equivalent magnetic particle diameter $\check{D}_n$ as a function of $\tilde{V}_v$ and $\tilde{V}_n$; and calculating a particle diameter dispersity value, $\bar{D}_d$, of the sample, as a function of the diameter values $\check{D}_v$ and $\check{D}_n$. The at least one first statistical parameter can include a statistical parameter known to those of ordinary skill in the art for the measurement of particles separated according to size. For non-limiting examples, the at least one first statistical parameter can include a statistical mean size of the nanoparticles, a standard size deviation of the nanoparticles, a statistical size range of the nanoparticles, a particle diameter dispersity value of the nanoparticles, and a combination of two or more of the aforementioned statistical parameters.

FIG. 3 also shows that in one embodiment, the apparatus 20 can include a computer controlled monitoring system 58 capable of determining and recording the at least one first statistical parameter about the nanoparticles circulating in the fluid stream according to one or more monitoring parameters. The monitoring parameters can include one or more test locations, one or more process times, and a combination of two or more of the aforementioned monitoring parameters.

In an additional embodiment, the apparatus can include a comparison system 59 configured for comparing the at least one first statistical parameter with a corresponding at least one second statistical parameter corresponding to a second size and size distribution for the nanoparticles in the sample of the fluid stream as measured and determined by DLS, TEM, SEM, and/or other non-magnetometry nanoparticle measurement methodologies. The comparison system can then be configured for calibrating the at least one first statistical parameter based upon the comparison.

Figure 6:
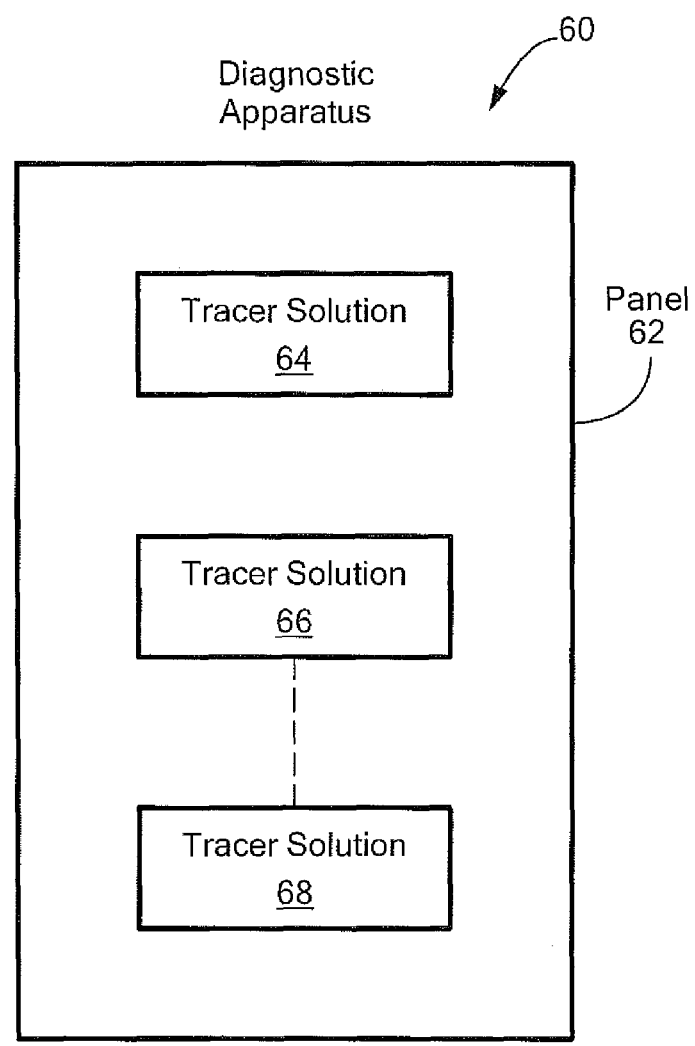
FIG. 6 is a functional block diagram of an embodiment of the present invention.

FIG. 6 shows a diagnostic apparatus 60 of the invention including a diagnostic series, array or panel 62 including at least two or more tracer solutions. In FIG. 6, the tracer solutions are shown as tracer solutions 64-68 in a non-limiting example. Each tracer solution can include a closely sized and/or non-randomly sized distribution of nanoparticles having a predetermined size and size distribution. The nanoparticles can include non-magnetic, partially magnetic, fully magnetic or superparamagnetic nanoparticles, and combinations thereof. The size of an individual nanoparticle can refer to an intrinsic core diameter measurement, a hydrodynamic diameter measurement, and a combination of intrinsic core diameter and hydrodynamic diameter measurements depending upon the application. The predetermined size and size distribution of the nanoparticles in a sample of the tracer solution can correspond to at least one first statistical parameter known to those of ordinary skill in the art such as, for example, a statistical mean size of the nanoparticles, a standard size deviation of the nanoparticles, a statistical size range of the nanoparticles, and a particle diameter dispersity value of the nanoparticles.

In another embodiment, the tracer solutions 64-68 can be arranged in the diagnostic panel 60 in a selected order according to the predetermined size and size distribution as defined by the at least one first statistical parameter. For example, the order can correspond to an increasing or decreasing statistical mean size, statistical size range, standard size deviation, and/or particle diameter dispersity value of the nanoparticles.

Figure 7:
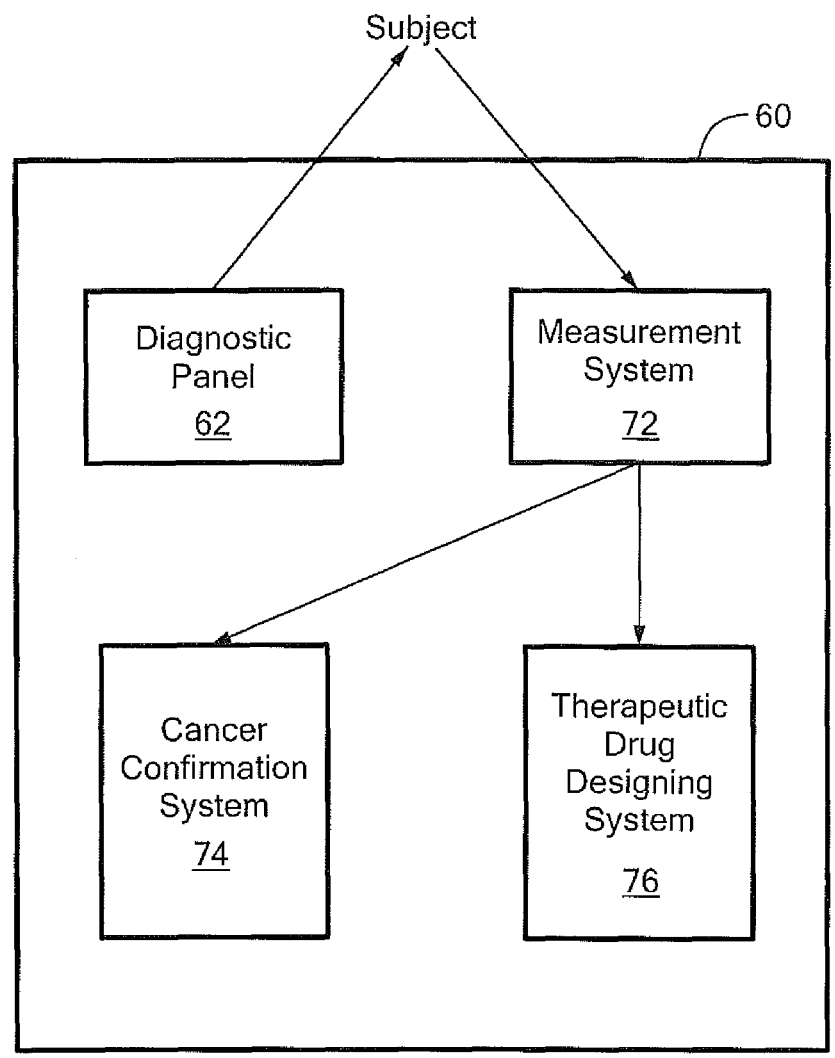
FIG. 7 is a functional block diagram of an embodiment of the present invention.

In another embodiment, as shown in FIG. 7, the diagnostic apparatus further includes a measurement system 72, wherein the selected order of the tracer solutions is adapted for detection and determination of at least one in situ measurement in the subject with the measurement system. The in situ measurement can include a size based ingestion rate of the nanoparticles by the subject, a progression profile of a physical structure of a target in the subject, a size based mapping of locations of the nanoparticles in the subject and/or the target, a size based take up rate of the nanoparticles by the subject and/or target, a size based flow rate of the nanoparticles through the subject and/or target, a retention rate of the nanoparticles by the subject and/or target, and/or target, a progression of a size of a defect in the subject and/or target, and a combination of two or more in situ measurements.

In another embodiment, as shown in FIG. 7, the diagnostic apparatus further includes a cancer confirmation system 74 for confirming the presence or absence of a cancer in the subject based on a correlation of the in situ measurement with the respective presence or absence of an EPR function. In an additional or alternative embodiment, the diagnostic apparatus includes a therapeutic drug designing system 76 configured for sizing a therapeutic agent molecule based upon a correlation of the in situ measurement with the presence of an EPR function; determining a geometric profile of a target tissue having the EPR function based upon the in situ measurement; and matching a physical dimension of the therapeutic agent molecule with the geometric profile of the target tissue having the EPR function to optimize delivery of the molecule to the target tissue.

In another aspect, the invention features a method for obtaining or producing a continuous fluid stream containing nanoparticles. A flow chart of the steps of the method is illustrated in FIG. 7. The method 70 includes providing a source of the fluid stream, wherein the fluid stream includes a randomly sized distribution of nanoparticles, step 72; receiving the fluid stream produced from the source in a flow control zone and controlling the fluid stream to produce a controlled fluid stream having a selected flow rate, step 74; receiving the controlled fluid stream in a separation zone and separating or segregating the controlled fluid stream into a separated fluid stream having at least one non-randomly sized distribution of nanoparticles, step 76; and receiving in a collection zone the separated fluid stream to produce at least one collected stream segregated according to the at least one non-randomly sized distribution of nanoparticles, step 78. Depending upon the embodiment of the method, the size of a nanoparticle can be defined in terms of the intrinsic core diameter, the hydrodynamic diameter, and a combination of the two diameters. The nanoparticles of the method can include non-magnetic, partially magnetic, fully magnetic or superparamagnetic nanoparticles, or a combination of at least two different nanoparticle types.

Figure 8:
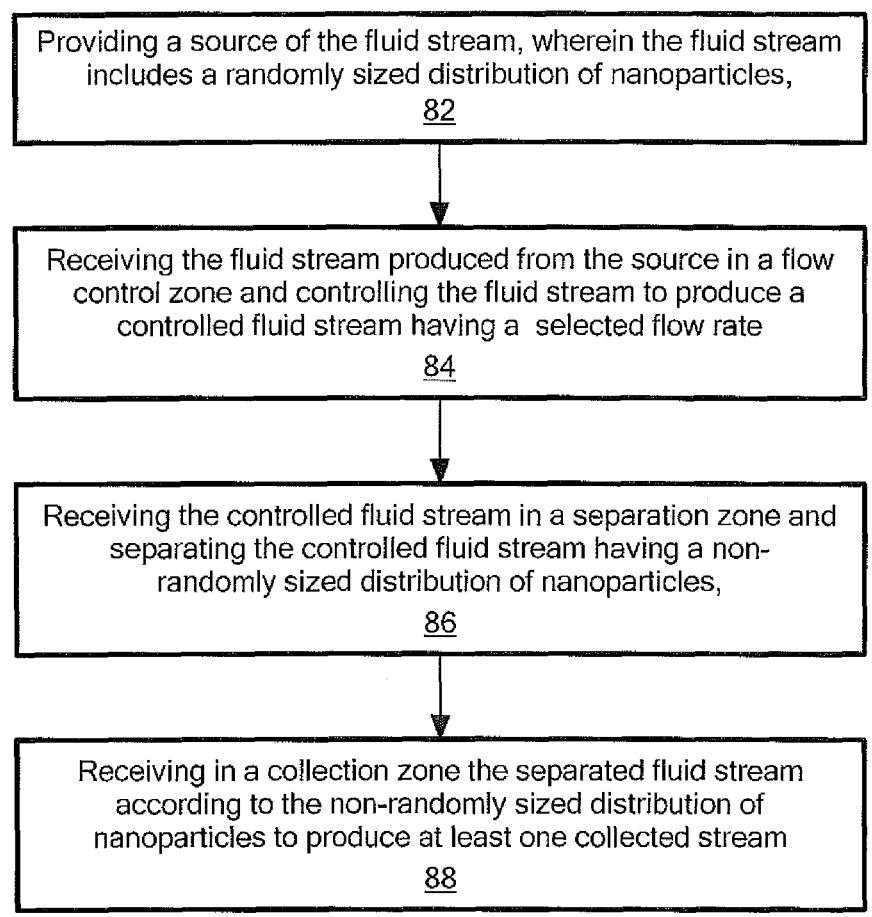
FIG. 8 is a flow chart of a method according to an embodiment of the present invention.
Figure 9:
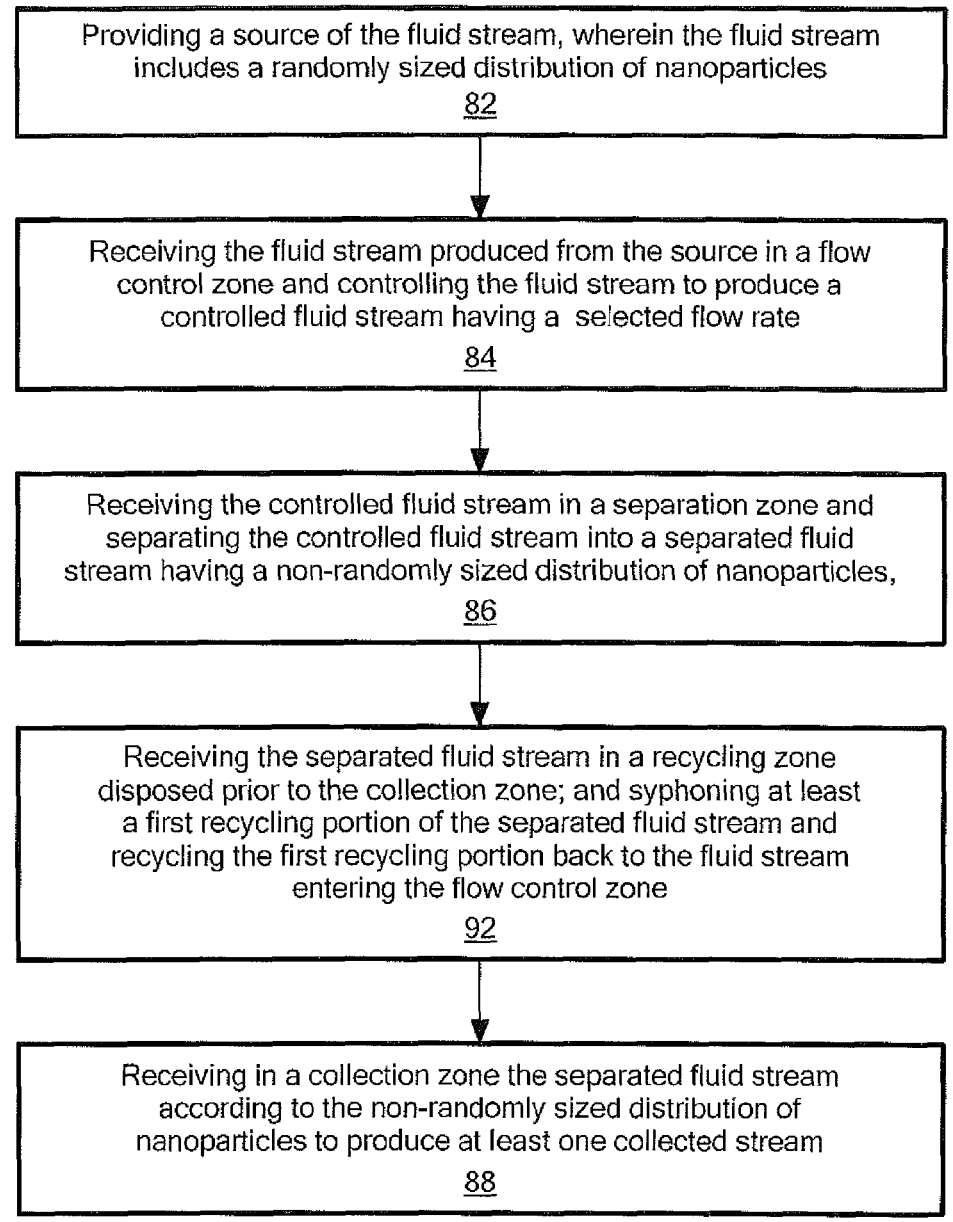
FIG. 9 is a flow chart of a method according to an embodiment of the present invention.

FIG. 8 illustrates the method of the invention including receiving the separated fluid stream in a recycling zone disposed prior to the collection zone, and syphoning at least a first recycling portion of the separated fluid stream and recycling the first recycling portion back to the fluid stream entering the flow control zone, step 80.

The method can also include controlling the fluid stream according to a viscosity of the fluid stream. The method can further include adapting the flow control zone for control by a flow control computer.

In different non-limiting embodiments, the method can include separating or segregating the controlled fluid stream using one or more non-magnetic separation systems and one or more magnetic separation systems, as described above. In a preferred embodiment, the controlled fluid stream is separated or segregated using a HGMS system.

In one embodiment, the method produces a fluid stream including at least partially magnetic nanoparticles. This method detects, determines and records at least one first statistical parameter corresponding to a first size and size distribution of the nanoparticles as defined by the computer implemented magnetometry method described above. The at least one first statistical parameter can include a statistical parameter known to those of ordinary skill in the art for the measurement of particles separated according to size. For non-limiting examples, the at least one first statistical parameter can include a statistical mean size of the nanoparticles, a standard size deviation of the nanoparticles, a statistical size range of the nanoparticles, and a particle diameter dispersity value of the nanoparticles.

In another embodiment, the method can include detecting and recording with a computer controlled monitoring system the at least one first statistical parameter corresponding to the first size and size distribution of the nanoparticles circulating in the fluid stream according to at least one monitoring parameter selected from the group consisting of one or more test locations in the apparatus, one or more process times, and a combination of two or more of the aforementioned monitoring parameters.

In another embodiment, the method can further include comparing the at least one first statistical parameter with a corresponding at least one second statistical parameter corresponding to a second size and size distribution of the nanoparticles as measured and determined with a non-magnetometry measurement method, such as, for non-limiting examples, DLS, TEM, and SEM; and calibrating the at least one first statistical parameter based upon the comparison.

In another embodiment, the method can include introducing the collected fluid stream into a subject; and correlating the non-randomly sized distribution of nanoparticles to an EPR effect of a tumor. The EPR effect can include at least one of a vasculature sizing change, a vasculature opening change, a vascular pathway change, a tumor extravasation, an uptake by a tumor, a retention by the tumor, and a densification of the tumor, a fluid flow change of the collected fluid stream in the subject, and a non-homogeneous physical change in a structure in the subject.

In a further embodiment, the method of the invention can include sequentially introducing at least a first collected stream and a second collected stream into a tumor; capturing an MRI image of the tumor after the introduction of each collected stream; comparing the captured MRI images to stored images, each stored image having a corresponding nanoparticle size and size distribution information as determined in accordance with the computer implemented magnetometry method discussed above; and determining the tumor vasculature as a function of the comparison; wherein the nanoparticles can include at last partially magnetic particles.

Additionally, the methods of the invention can be used to determine individual therapeutic protocols for cancer or other diseases because the correlation between sized magnetic nanoparticle tracers and their EPR effect can be predictive of individual response to nanoscale therapeutics.

The methods of the invention can be used to analyze organs, tumors, and vasculature sub-structure. This analysis can be used for the diagnostic profiling of nanoparticle size and sized capture and for determining EPR effects, which in turn can be used for monitoring specific disease progression and specific targeted therapy. This analysis can also be used for therapeutic effect profiling of nanoparticle size and sized capture and for determining individual EPR effects which in turn can be used for pre- and post-targeted therapy studies. The systems and methods of the invention related to diagnostic panels employing at least partially magnetic nanoparticles can be used for discriminating between active and non-active cancers by MRI measurement of EPR dynamics or effects that are exclusive to active cancers.

In embodiments for medical applications including pharmaceutical applications, closely sized and/or non-randomly sized distributions of at least partially magnetic nanoparticles can be controlled in-situ by internal and/or external magnetic fields. The nanoparticles can be introduced orally or by injection, into a subject, and in-situ observation of various organs of interest can be accomplished with MRI. Nanoparticles which are pre-treated with a surface dye can be observed by alternative detection systems.

In embodiments where series, arrays or panels of closely sized and/or non-randomly sized distributions of nanoparticles are introduced into a subject, non-invasive detection systems can be used to determine presence, concentrations, mobility, organ aperture profiling and functionality, residual lifetimes and clearance status for diagnostic purposes.

Figure 10:
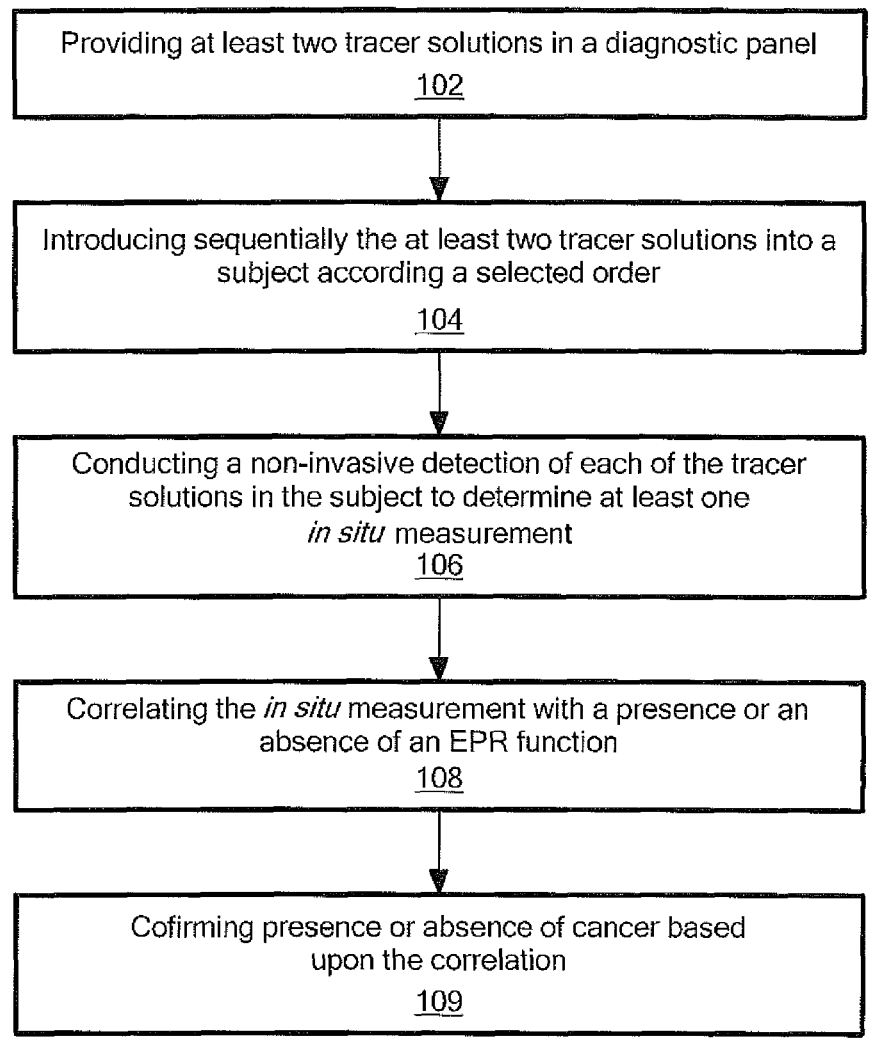
FIG. 10 is a flow chart of a method according to an embodiment of the present invention.

For example, in one embodiment, as shown in FIG. 10, invention features a method 100 including the following steps: providing at least two tracer solutions in a diagnostic panel, step 102; introducing sequentially the at least two tracer solutions into a subject according to a selected order, step 104; conducting a non-invasive detection of each of the tracer solutions in the subject to determine at least one in situ measurement step 106; correlating the in situ measurement with a presence or an absence of an EPR function, step 108; and confirming the presence or absence of cancer based upon the correlation, step 109.

Figure 11:
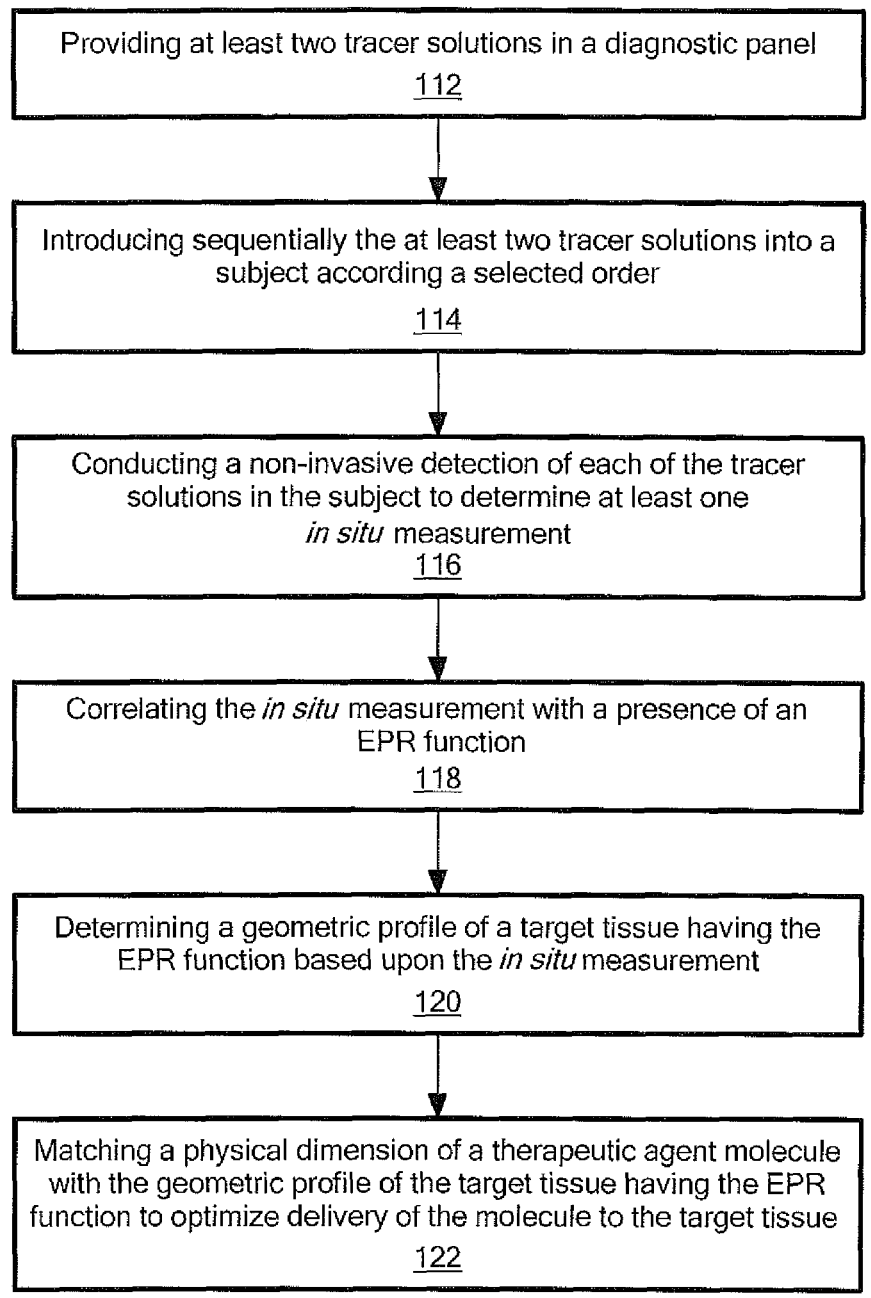
FIG. 11 is a flow chart of a method according to an embodiment of the present invention.

In an alternative or additional embodiment, as shown in FIG. 11, the invention features a method 110 including providing at least two tracer solutions in a diagnostic panel, step 112; introducing sequentially the at least two tracer solutions into a subject according a selected order, step 114; conducting a non-invasive detection of each of the tracer solutions in the subject to determine at least one in situ measurement, step 116; correlating the in situ measurement with a presence of an EPR function, step 118; determining a geometric profile of a target tissue having the EPR function based upon the in situ measurement, step 120; and matching a physical dimension of a therapeutic agent molecule with the geometric profile of the target tissue having the EPR function to optimize delivery of the molecule to the target tissue, step 122.

In other embodiments of in-situ closely sized and/or non-randomly sized distributions of nanoparticles with and without fluorescent dye surface pretreatment, alternative non-invasive external detection system can be used to determine therapeutic treatment efficacy, change and efficiency of targeted drug delivery.

In still another embodiment, the localization of closely sized and/or non-randomly sized distributions of at least partially magnetic nanoparticles can be regionally and locally enhanced by internal or external magnetic fields for non-invasive viewing.

In further embodiments, nonmagnetic and/or partially magnetic closely sized and/or non-randomly sized distributions of nanoparticles, which are regulated and controlled by body fluids, can be treated with fluorescent dye pretreatments and alternative non-magnetic, non-invasive detection systems can be used for control, enhancement and study of the nanoparticles.

The foregoing examples and detailed description are not to be deemed limiting of the invention which is defined by the following claims. The invention is understood to encompass such obvious modifications thereof as would be apparent to those of ordinary skill in the art.

What is claimed is:
1. An apparatus for producing a fluid stream having plurality of nanoparticles in the fluid stream comprising:
   a source configured to provide a fluid stream having a first randomly sized distribution of a plurality of nanoparticles;

a flow control zone configured to receive the fluid stream from the source and to control the fluid stream to produce a controlled fluid stream having a selected flow rate;

a separation zone configured to receive and to separate the selectively controlled fluid stream into at least one separated fluid stream having a non-randomly sized distribution of nanoparticles; and a collection zone capable of receiving the separated fluid stream according to at least one non-random sized distribution of nanoparticles to produce at least one collected stream;

wherein the apparatus is configured for a continuous flow of the fluid stream;

wherein a size of a nanoparticle is related to at least one of a group of nanoparticle size measurements including an intrinsic core diameter, a hydrodynamic diameter, and a combination of intrinsic core diameter and hydrodynamic diameter measurements; and wherein the nanoparticles are selected from a group of nanoparticle types consisting of non-magnetic nanoparticles, partially magnetic nanoparticles, magnetic nanoparticles, superparamagnetic nanoparticles, and a combination of at least two different nanoparticle types.

2. The apparatus of claim 1 further comprising a recycling zone capable of receiving the separated fluid stream prior to the collection zone, and syphoning and recycling at least a first recycling portion of the separated fluid stream back to the fluid stream provided from the source prior to the fluid stream entering the flow control zone.

3. The apparatus of claim 1, wherein the flow control zone further comprises an element capable of controlling the fluid stream according to a viscosity of the fluid stream.

4. The apparatus of claim 1, wherein the flow control zone is adapted for control by a flow control computer.

5. The apparatus of claim 1,
wherein the separation zone comprises at least one non-magnetic separation system; and
wherein the non-magnetic separation system is selected from a group of non-magnetic separation systems consisting of one or more mechanical pre-filtering mechanical separation systems, one or more gravitational filtering mechanical separation systems, one or more liquid chromatography separation systems, and a combination of two or more of the aforementioned non-magnetic separation systems.

6. The apparatus of claim 5,
wherein separation zone comprises at least one magnetic separation system; and
wherein the magnetic separation system is selected from a group of magnetic separation systems consisting of one or more static magnetic separation systems configured to produce a uniform magnetic field, one or more pulsating direct current magnetic separation systems configured to produce a pulsed magnetic field and having current flowing in one direction, one or more pulsating alternating current magnetic separation systems configured to produce a pulsed magnetic field having current flowing in alternating directions, one or more variable gradient magnetic separation elements configured to produce at least two magnetic fields having different gradients, and a combinations of two or more of the aforementioned magnetic separation systems.

7. The apparatus of claim 5, wherein the separation zone comprises at least one high gradient magnetic separation system.

8. The apparatus of claim 1 further comprising
a computer implemented magnetometry system capable detecting, determining and recording at least one first statistical parameter corresponding to a selected size and size distribution of the nanoparticles in a sample of the fluid stream, wherein the size and size distribution is defined by a computer implemented magnetometry method employing the following steps:

performing a magnetic measurement analysis of the sample and generating magnetization data therefrom;

determining an asymptotic portion of high field data from the magnetization data for each of four branches (A,B,C,D) as $M_H$ vs. 1/H where $M_H$ is the measured magnetization in a magnetic field of intensity H approaching its saturation value;

performing a linear regression analysis of the data in each branch and generating a first correlation curve of the form $M_H = \alpha/H + \beta$;

calculating both a number average particle volume, $\tilde{V}_n$, and a saturation magnetization, $M_{sat}$, of the sample, as a function of the first correlation curve;

combining low field, linear data of $M_H$ for branches A and C, and branches B and D, and obtaining two plots of $M_H$ vs. H for values of H within a range from −50 Oe to +50 Oe;

performing a linear regression analysis of the data in each branch combination and generating a second correlation curve of the form $M_H = \gamma H + \beta$;

calculating a volume average particle volume $\tilde{V}_v$ as a function of the saturation magnetization value $M_{sat}$ obtained from the high field measurements, and using the value of the slope $\gamma$ for the ratio of $M_H/H$;

calculating a volume average spherical equivalent magnetic particle diameter $\check{D}_v$ and a number average spherical equivalent magnetic particle diameter $\check{D}_n$ as a function of $\tilde{V}_v$ and $\tilde{V}_n$; and calculating a particle diameter dispersity value, $D_d$, of the sample, as a function of the diameter values $\check{D}_v$ and $\check{D}_n$;

wherein the nanoparticles include a plurality of at least partially magnetic nanoparticles; and wherein the at least one first statistical parameter is selected from the group consisting of a statistical mean size of the nanoparticles, a standard size deviation of the nanoparticles, a statistical size range of the nanoparticles, and the particle diameter dispersity value of the nanoparticles.

9. The apparatus of claim 8 further comprising
a computer controlled monitoring system capable of detecting, determining and recording the at least one first statistical parameter corresponding to the nanoparticles circulating in the fluid stream according to at least one monitoring parameter;

wherein the monitoring parameter is selected from the group consisting of one or more test locations in the apparatus, one or more process times, and a combination of two or more monitoring the aforementioned parameters.

10. The apparatus of claim 9 further comprising
a comparison system configured for comparing the at least one first statistical parameter with a corresponding at least one second statistical parameter corresponding to a second size and distribution of the nanoparticles circulating in the fluid stream as detected and determined by a non-magnetometry measurement;

wherein the comparison system is configured for calibrating the at least one first statistical parameter based upon the comparison.

11. The apparatus of claim 1, wherein upon introduction into a subject, the collected stream is characterized as having a distinguishable behavior as compared to the fluid stream having the first randomly sized distribution of nanoparticles.

12. A diagnostic apparatus comprising:
a diagnostic panel including at least two tracer solutions configured for introduction into a subject;
wherein each of the tracer solutions has a non-randomly sized distribution of a plurality of nanoparticles;
wherein each of the non-randomly sized distributions corresponds to at least one first statistical parameter selected from the group consisting of a statistical mean size of the nanoparticles, a standard size deviation of the nanoparticles, a statistical size range of the nanoparticles, a particle diameter dispersity value of the nanoparticles, and a combination of at least two of the aforementioned statistical parameters;
wherein a size of a nanoparticle is related to one of group of nanoparticle size measurements including an intrinsic core diameter, a hydrodynamic diameter, and a combination of an intrinsic core diameter and a hydrodynamic diameter; and
wherein the nanoparticles are selected from a group of nanoparticle types consisting of non-magnetic nanoparticles, partially magnetic nanoparticles, magnetic nanoparticles, superparamagnetic nanoparticles, and a combination of at least two different nanoparticle types.

13. The diagnostic apparatus of claim 12,
wherein the tracer solutions are organized in the diagnostic panel in a selected order according to the at least one first statistical parameter for a sequential introduction into the subject according to the selected order.

14. The diagnostic apparatus of claim 12 further comprising
a measurement system;
wherein the selected order and the sequential introduction of the tracer solutions in the selected order is adapted for a non-invasive detection of at least one in situ measurement in the subject with the measurement system;
wherein the in situ measurement is selected from the group of in situ measurements consisting of a size based ingestion rate of the nanoparticles by the subject, a size based mapping of locations of the nanoparticles in the subject, a size based take up rate of the nanoparticles by the subject, a size based flow rate of the nanoparticles through the subject, a retention rate of the nanoparticles by the subject, a progression profile of a size of a physical structure in the subject, a progression profile of a size of a defect in the subject, and a combination of two or more in situ measurements.

15. The diagnostic apparatus of claim 14 further comprising
a cancer confirmation system configured for confirming a presence or an absence of a cancer in the subject based upon a confirmation method including the steps of
correlating the in situ measurement with a presence of at least one EPR function or an absence of the EPR function in the subject;
confirming a presence or an absence of a cancer in the subject based upon the correlation of the in situ measurement with, respectively, the presence or the absence of the EPR function;
wherein the EPR function is selected from a group of functions consisting of an altered vasculature sizing, an altered vasculature opening, an altered vascular pathway, an extravasation of a tissue, an uptake of the nanoparticles, a retention of the nanoparticles, and a densification of a tissue, a size based change in a fluid flow rate of the nanoparticles, a non-homogeneous physical change in the subject, and a combination of two or more functions.

16. The diagnostic apparatus of claim 14 further comprising
a therapeutic drug designing system configured for sizing a therapeutic agent molecule based upon a designing method including the steps of:
correlating the in situ measurement with a presence of at least one EPR function in the subject;
determining a geometric profile of a target tissue having the EPR function based upon the in situ measurement; and
matching a physical dimension of the therapeutic agent molecule with the geometric profile of the target tissue having the EPR function to optimize delivery of the molecule to the target tissue;
wherein the EPR function is selected from a group of functions consisting of an altered vasculature sizing, an altered vasculature opening, an altered vascular pathway, an extravasation of a tissue, an uptake of the nanoparticles, a retention of the nanoparticles, and a densification of a tissue, a size based change in a fluid flow rate of the nanoparticles, a non-homogeneous physical change in the subject, and a combination of two or more functions.

\* \* \* \* \*